(12) United States Patent
Helfman et al.

(10) Patent No.: US 8,451,272 B2
(45) Date of Patent: May 28, 2013

(54) TIME EXPANSION FOR DISPLAYING PATH INFORMATION

(75) Inventors: Jonathan Helfman, Half Moon Bay, CA (US); Joseph H. Goldberg, San Carlos, CA (US)

(73) Assignee: Oracle International Corporation, Redwood Shores, CA (US)

(*) Notice: Subject to any disclaimer, the term of this patent is extended or adjusted under 35 U.S.C. 154(b) by 798 days.

(21) Appl. No.: 12/615,763

(22) Filed: Nov. 10, 2009

(65) Prior Publication Data

US 2010/0119111 A1 May 13, 2010

Related U.S. Application Data

(60) Provisional application No. 61/113,538, filed on Nov. 11, 2008.

(51) Int. Cl.
*G06T 11/20* (2006.01)
*G06T 13/00* (2011.01)

(52) U.S. Cl.
USPC .......................................... 345/440; 345/475

(58) Field of Classification Search
USPC ................................................ 345/440, 475
See application file for complete search history.

(56) References Cited

U.S. PATENT DOCUMENTS

| | | | |
|---|---|---|---|
| 4,859,050 A | 8/1989 | Borah et al. | |
| 4,973,149 A | 11/1990 | Hutchinson | |
| 5,517,021 A | 5/1996 | Kaufman et al. | |
| 5,649,061 A | 7/1997 | Smyth | |
| 5,726,916 A | 3/1998 | Smyth | |
| 6,381,339 B1 | 4/2002 | Brown et al. | |
| 6,755,527 B1 | 6/2004 | Goldberg | |
| 7,136,073 B2 | 11/2006 | Newman | |
| 7,339,580 B2 | 3/2008 | Westerman et al. | |
| 7,561,143 B1 | 7/2009 | Milekic | |
| 7,881,493 B1 | 2/2011 | Edwards et al. | |
| 7,922,670 B2 | 4/2011 | Jones et al. | |
| 2008/0222562 A1 | 9/2008 | Helfman et al. | |
| 2009/0043504 A1 | 2/2009 | Bandyopadhyay et al. | |
| 2010/0118030 A1 | 5/2010 | Helfman et al. | |
| 2010/0118032 A1 | 5/2010 | Helfman et al. | |

(Continued)

OTHER PUBLICATIONS

Franklin et al., A Path Based Model for Sonification, Proceeding of the Eighth Internation Conference on Information Visualisation, Jul. 2004, pp. 1-6.*

(Continued)

*Primary Examiner* — M Good Johnson
(74) *Attorney, Agent, or Firm* — Kilpatrick Townsend & Stockton LLP

(57) ABSTRACT

Embodiments of the present invention provide systems and methods for displaying sequential information representing a path. The sequential information can include a number of tokens representing a path. A representation of the tokens and path of the sequential information can be displayed. An instruction to adjust the representation of the path of the sequential information can be received. For example, instruction can comprise user instruction, including but not limited to a user manipulation of a slider control of a user interface through which the representation of the sequence is displayed. The displayed representation of the path of the sequential information can be updated based on and corresponding to the instruction. So for example, the user can click and drag or otherwise manipulate the slider control above and the displayed representation of the path can be expanded and/or contracted based on the user's movement of the slider control.

22 Claims, 9 Drawing Sheets

U.S. PATENT DOCUMENTS

2010/0118267 A1 5/2010 Helfman et al.
2010/0119112 A1 5/2010 Helfman et al.
2010/0121812 A1 5/2010 Helfman et al.

OTHER PUBLICATIONS

Tobii Eye Tracking, "Tobii Eye Tracking: Research with Vision," 8 pages downloaded on Dec. 28, 2009 at URL: www.tobii.com.
Tobii Studio 2 brochure, "Comprehensive Eye Tracking analysis & visualization software," 5 pages downloaded on Dec. 28, 2009 at URL: www.tobii.com.
Tobii® Technology, "Tobii StudioTM Tobii Technology," Product Description, Revision 2.0, May 2009, pp. 1-26 downloaded on Dec. 28, 2009 at URL: www.tobii.com.
Tobii® Technology, "Tobii T/X series Eye Trackers," Product Description, Revision 2.0, May 2009, pp. 1-22 downloaded on Dec. 28, 2009 at URL: www.tobii.com.
U.S. Appl. No. 12/615,736, filed Nov. 10, 2009, Helfman et al.
U.S. Appl. No. 12/615,749, filed Nov. 10, 2009, Helfman et al.
U.S. Appl. No. 12/616,016, filed Nov. 10, 2009, Helfman et al.
U.S. Appl. No. 12/616,030, filed Nov. 10, 2009, Helfman et al.
U.S. Appl. No. 12/616,035, filed Nov. 10, 2009, Helfman et al.
Tobii T60 & T120 Eye Trackers, "Plug & Play Eye Trackers for On-Screen Research," 2 pages downloaded on Dec. 28, 2009 at URL: www.tobii.com.
Tobii T60 XI Eye Tracker, "Widescreen Eye Tracker for large stimulus display," 2 pages downloaded on Dec. 28, 2009 at URL: www.tobii.com.
Tobii X60 & X120 Eye Tracker, "Flexible Eye Trackers for Studies of Physical Objects," 2 pages downloaded on Dec. 28, 2009 at URL: www.tobii.com.
Aula, A., et al., "Eye-tracking Reveals the Personal Styles for Search Result Evaluation," in Proceedings of Human-Computer Interaction, pp. 135-138, Tampere Unit for Computer-Human Interaction (TAUCHI).
Aula, A., et al., "Multilingual Search Strategies," in Proceedings of CHI 2009—Spotlight on Works in Progress—Session 1, Boston, MA, USA, Apr. 4-9, 2009, pp. 3865-3870, ACM Press, Copyright 2009.
Beymer, D., et al., "WebGazeAnalyzer: A System for Capturing and Analyzing Web Reading Behavior Using Eye Gaze," in Proceedings of CHI 2005, Portland, Oregon, USA, Apr. 2-7, 2005, pp. 1913-1916, ACM Press, Copyright 2005.
Bednarik, R., et al., "Temporal Eye-Tracking Data: Evolution of Debugging Strategies with Multiple Representations," in proceedings of 2008 Symposium on Eye Tracking Research & Applications, Savannah, Georgia, Mar. 26-28, 2008, pp. 99-102, ACM Press, Copyright 2008.
Bojko, A., "Informative or Misleading? Heatmaps Deconstructed," J.A. Jacko (Ed.): Human-Computer Interaction, Part I, HCII 2009, LNCS 5610, 2009, pp. 30-39, Springer-Verlag Berlin Heidelberg.
Bojko, A., "Using Eye Tracking to Compare Web Page Designs: A Case Study," Journal of Usability Studies, May 2006, pp. 112-120, Issue 3, vol. 1.
Church, K., et al., "Dotplot: a Program for Exploring Self-Similarity in Millions of Lines of Text and Code," The Journal of Computational and Graphical Statistics, 1993, 12 pages (pp. 153-174 in publication), vol. 2, No. 2.
Cinar, M., "Eye Tracking Method to Compare the Usability of University Web Sites: A Case Study," M. Kurosu (Ed.): Human Centered Design, HCII 2009, LNCS 5619, 2009, pp. 671-678, Springer-Verlag Berlin Heidelberg.
Cutrell, E., et al., "What Are You Looking For? An Eye-tracking Study of Information Usage in Web Search," in Proceedings of CHI 2007, San Jose, California, USA, Apr. 28-May 3, 2007, 10 pages (pp. 407-416 in publication), ACM, Copyright 2007.
"Eyetools Eyetracking Research: But what does it all mean? Understanding eye-tracking results (Part 4)," Sep. 6, 2007, pp. 1-3, downloaded on Mar. 19, 2009 at URL: http://blog.eyetools.net/eyetools_research/2007/09/but-what-does-2.html.
Feusner, M., et al., "Testing for Statistically Significant Differences Between Groups of Scan Patterns," in Proceedings of 2008 Symposium on Eye Tracking Research & Applications, Savannah, Georgia, Mar. 26-28, 2008, pp. 43-46, ACM Press, Copyright 2008.
Goldberg, J. H., et al., "Computer Interface Evaluation Using Eye Movements: Methods and Constructs," International Journal of Industrial Ergonomics, 1999, pp. 631-645, vol. 24.
Goldberg, J. H., et al., "Eye Movement-Based Evaluation of the Computer Interface," Advances in Occupational Ergonomics and Safety, S. Kumar, (Ed.), 1998, pp. 529-532, IOS Press.
Goldberg, J. H., et al., "Eye Tracking in Web Search Tasks: Design Implications," in Proceedings of 2002 Symposium on Eye Tracking Research & Applications, ACM Press, 2002, 8 pages.
Goldberg, J. H., et al., "Scanpath Clustering and Aggregation," Applications User Experience, Oracle USA, 8 pages.
Goldberg, J. H., et al., "Visual Scanpath Representation," Applications User Experience, Oracle USA, 8 pages.
Granka, L., et al., "Incorporating Eyetracking into User Studies at Google," Workshop paper presented at CHI 2006, 2006, 2 pages, ACM Press.
Granka, L., et al., "Location Location Location: Viewing Patterns on WWW Pages," in Proceedings of the 2006 Symposium on Eye Tracking Research & Applications, San Diego, California, Mar. 27-29, 2006, p. 43, ACM Press, Copyright 2006.
Guan, Z., et al., "An Eye Tracking Study of the Effect of Target Rank on Web Search," in Proceedings of CHI 2007, San Jose, California, USA, Apr. 28-May 3, 2007, 4 pages (pp. 417-420 in publication), ACM Press, Copyright 2007.
Habuchi, Y., et al., "Comparison of Eye Movements in Searching for Easy-to-Find and Hard-to-Find Information in a Hierarchically Organized Information Structure," in Proceedings of the 2008 Symposium on Eye Tracking Research & Applications, Savannah, Georgia, Mar. 26-28, 2008, pp. 131-134, ACM Press, Copyright 2008.
Harris, R. L., "Information Graphics: A Comprehensive Illustrated Reference," 1999, pp. 164-177 and p. 191, Management Graphics, Atlanta, GA, Oxford University Press, New York, Copyright 1999.
Helfman, J. I., "Dotplot Patterns: A Literal Look at Pattern Languages," TAPOS, 2(1):31-41, 1995.
Helfman, J. I., "Similarity Patterns in Language," Proceedings of the IEEE Symposium on Visual Language, 1994, 3 pages (pp. 173-175 in publication), IEEE Press.
Hembrooke, H., et al., "Averaging Scan Patterns and What They Can Tell Us," in Proceedings of the 2006 symposium on Eye Tracking Research & Applications, San Diego, California, Mar. 27-29, 2006, p. 41, ACM Press, Copyright 2006.
Heminghous, J., et al., "iComp: A Tool for Scanpath Visualization and Comparison," in Proceedings of the 2006 Applied Perception in Graphics and Visualization, Boston, Massachusetts, Jul. 28-29, 2006, p. 152, ACM Press, Copyright 2006.
Hornof, A. J., "Cognitive Strategies and Eye Movements for Searching Hierarchical Computer Displays," Paper: Modeling User Behavior, in Proceedings of CHI 2003, Ft. Lauderdale, Florida, USA, Apr. 5-10, 2003, pp. 249-256, CHI 2003: New Horizons, vol. No. 5, Issue No. 1, ACM Press, Copyright 2003.
Huang, Y., et al., "Rapid and Sensitive Dot-matrix Methods for Genome Analysis," Bioinformatics Advance Access, Jan. 22, 2004, pp. 460-466, vol. 20, No. 4, Oxford University Press, Copyright 2004, downloaded on Mar. 15, 2010 from URL :http://bioinformatics.oxfordjournals.org.
Josephson, S., et al., "Visual Attention to Repeated Internet Images: Testing the Scanpath Theory on the World Wide Web," in Proceedings of the 2002 Symposium on Eye Tracking Research & Applications, New Orleans, Louisiana, USA, pp. 43-49, ACM Press, Copyright 2002.
Levenshtein, V. I., "Binary Codes Capable of Correcting Deletions, Insertions, and Reversals," Cybernetics and Control Theory, Doklady Physics, Feb. 1966, pp. 707-710, vol. 10, No. 8.
Lorigo, L., et al., "Eye Tracking and Online Search: Lessons Learned and Challenges Ahead," Journal of the American Society for Information Science and Technology, 2008, pp. 1041-1052, vol. 59, No. 7, Copyright 2008.
Mankowski, W. C., et al., "Finding Canonical Behaviors in User Protocols," in Proceedings of CHI 2009, Boston, MA, USA, Apr. 4-9, 2009, 4 pages, ACM Press, Copyright 2009.

Marshall, S. P., "Identifying Cognitive State from Eye Metrics," Aviation, Space, and Environmental Medicine, May 2007, pp. B165-B186, vol. 78, No. 5, Section II.

Matsuda, Y., et al., "An Analysis of Eye Movements During Browsing Multiple Search Results Pages," J.A. Jacko (Ed.): Human-Computer Interaction, Part I, HCII, LNCS 5610, pp. 121-130, Copyright 2009 Springer-Verlag Berlin Heidelberg, Copyright 2009.

Myers, C. W., "Toward a Method of Objectively Determining Scanpath Similarity," [Abstract], Journal of Vision, Sep. 23, 2005, 2 pages, vol. 5, No. 8, Abstract 693, downloaded on Jan. 5, 2010 from URL: http://www.journalof vision.org/5/8/693/.

Najemnik, J., et al., "Optimal Eye Movement Strategies in Visual Search," Nature, Mar. 17, 2005, pp. 387-391, vol. 434, Copyright 2005 Nature Publishing Group.

Raiha, K., et al., "Static Visualization of Temporal Eye-Tracking Data," M.F. Costabile and F. Paterno (Eds.): Interact 2005, LNCS 3585, 2005, pp. 946-949, Copyright IFIP International Federation for Information Processing 2005.

Rantala, H., "Eye2i: Coordinated Multiple Views for Gaze Data," in Proceedings of the 2008 Symposium on Eye Tracking Research & Applications, Savannah, Georgia, Mar. 26-28, 2008, pp. 147-148, ACM Press, Copyright 2008.

Salvucci, D. D., et al., "Identifying Fixations and Saccades in Eye-Tracking Protocols," in Proceedings of the 2000 Symposium on Eye Tracking Research & Applications, Palm Beach Gardens, FL, USA, pp. 71-78, ACM Press, Copyright 2000.

Santella, A., et al., "Robust Clustering of Eye Movement Recordings for Quantification of Visual Interest," in Proceedings of the 2004 Symposium on Eye Tracking Research & Applications, San Antonio, Texas, 2004, pp. 27-34, ACM Press, Copyright 2004.

Smith, T. F., et al., "Identification of Common Molecular Subsequences," Reprinted from Journal of Molecular Biology, 1981, pp. 195-197, vol. 147, Academic Press, Copyright 1980.

Tufte, E. R., "Beautiful Evidence," Sparklines: Intense Word-Sized Graphics, Graphic Press LLC, Cheshire, CT., pp. 46-63, Copyright 2006.

Tufte, E. R., "The Visual Display of Quantitative Information," Theory of Data Graphics, Graphic Press LLC, Cheshire, CT., pp. 170-175, Copyright 1983.

Uwano, H., et al., "Analyzing Individual Performance of Source Code Review Using Reviewers' Eye Movement," in Proceedings of 2006 Eye Tracking Research & Applications, San Diego, California, Mar. 27-29, pp. 133-140, ACM Press.

Wattenberg, M., "Arc Diagrams: Visualizing Structure in Strings," in Proceedings of the IEEE Symposium on Information Visualization (InfoVis'02), 2002, 8 pages, IEEE Computer Society.

Werman, M., et al., "A Bayesian Method for Fitting Parametric and Nonparametric Models to Noisy Data," IEEE Transactions on Pattern Analysis and Machine Intelligence, May 2001, pp. 528-534, vol. 23, No. 5, Copyright 2001.

West, J. M., et al., "EyePatterns: Software for Identifying Patterns and Similarities Across Fixation Sequences," in Proceedings of the 2006 Symposium on Eye Tracking Research & Applications, San Diego, California, Mar. 27-29, 2006, pp. 149-154, ACM Press, Copyright 2006.

Wooding, D. S., "Eye Movements of Large Populations: II. Deriving Regions of Interest, Coverage, and Similarity Using Fixation Maps," Behavior Research Methods, Instruments, & Computers, 2002, pp. 518-528, vol. 34, No. 4, Psychonomic Society, Inc., Copyright 2002.

Aula, A., et al., "Eye-tracking Reveals the Personal Styles for Search Result Evaluation," in Proceedings of Human-Computer Interaction, Tampere Unit for Computer-Human Interaction (TAUCHI), 2005, pp. 135-138, [Can also be found in Proceedings of Interact 2005, Int. Fed. Info Proc., pp. 1058-1061.]

Goldberg, J. H., et al., "Scanpath Clustering and Aggregation," Applications User Experience, Oracle USA, 8 pages, Proceedings of the Mar. 2010 Eye Tracking Research and Applications, ACM Press.

Goldberg, J. H., et al., "Visual Scanpath Representation," Applications User Experience, Oracle USA, 8 pages, Proceedings of the Mar. 2010 Eye Tracking Research and Applications, ACM Press.

Duchowski, A., "Eye-Based Interaction in Graphical Systems: Theory & Practice," Siggraph 2000, 25 pages.

Torstling, A., "The Mean Gaze Path: Information Reduction and Non-Intrusive Attention Detection for Eye Tracking," Masters Degree Project, KTH Royal Institute of Technology, Stockholm, Sweden, Oct. 17, 2007, 64 pages.

U.S. Appl. No. 12/615,736, filed Nov. 10, 2009, Office Action mailed May 24, 2012, 4 pages.

U.S. Appl. No. 12/616,016, filed Nov. 10, 2009, Office Action mailed Jun. 20, 2012, 9 pages.

U.S. Appl. No. 12/616,030, filed Nov. 10, 2009, Office Action mailed Jul. 20, 2012, 11 pages.

U.S. Appl. No. 12/616,035, filed Nov. 10, 2009, Office Action mailed Jul. 23, 2012, 10 pages.

* cited by examiner

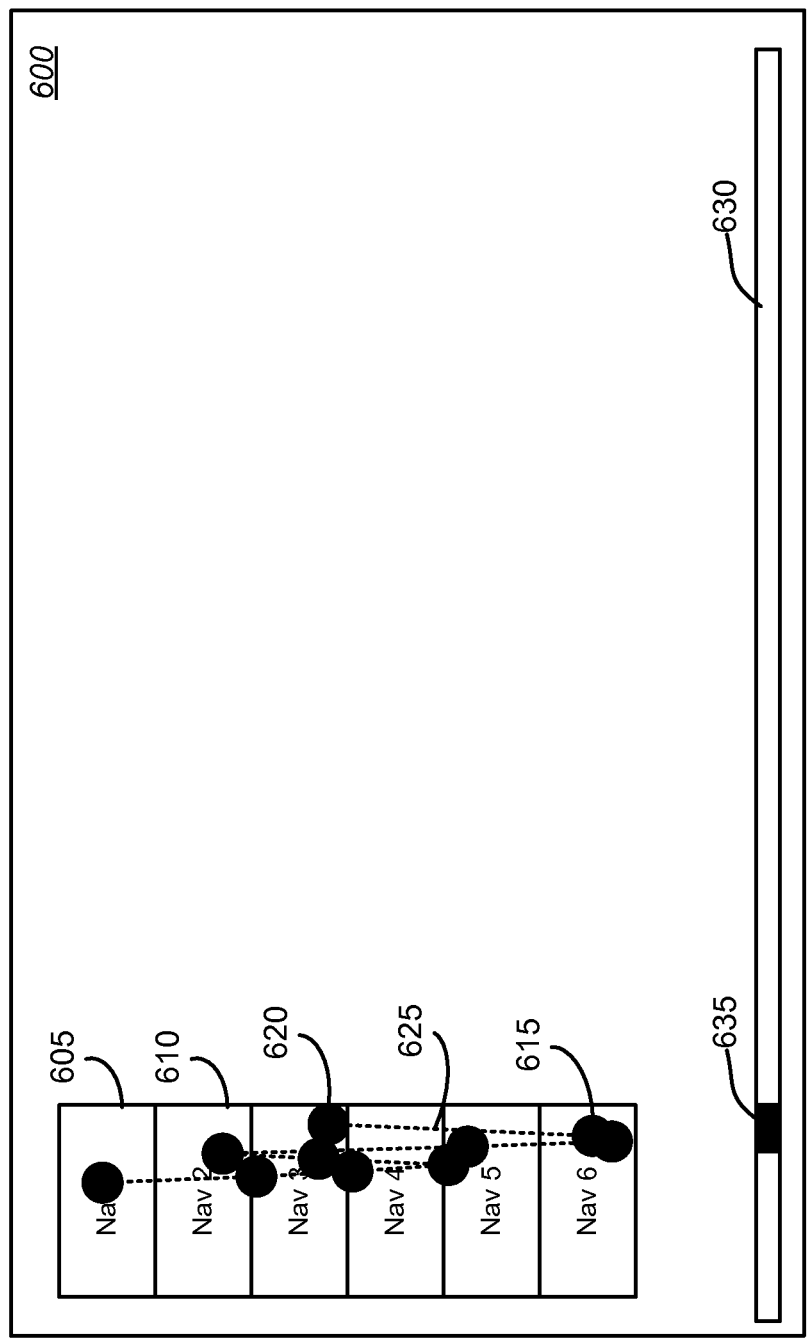

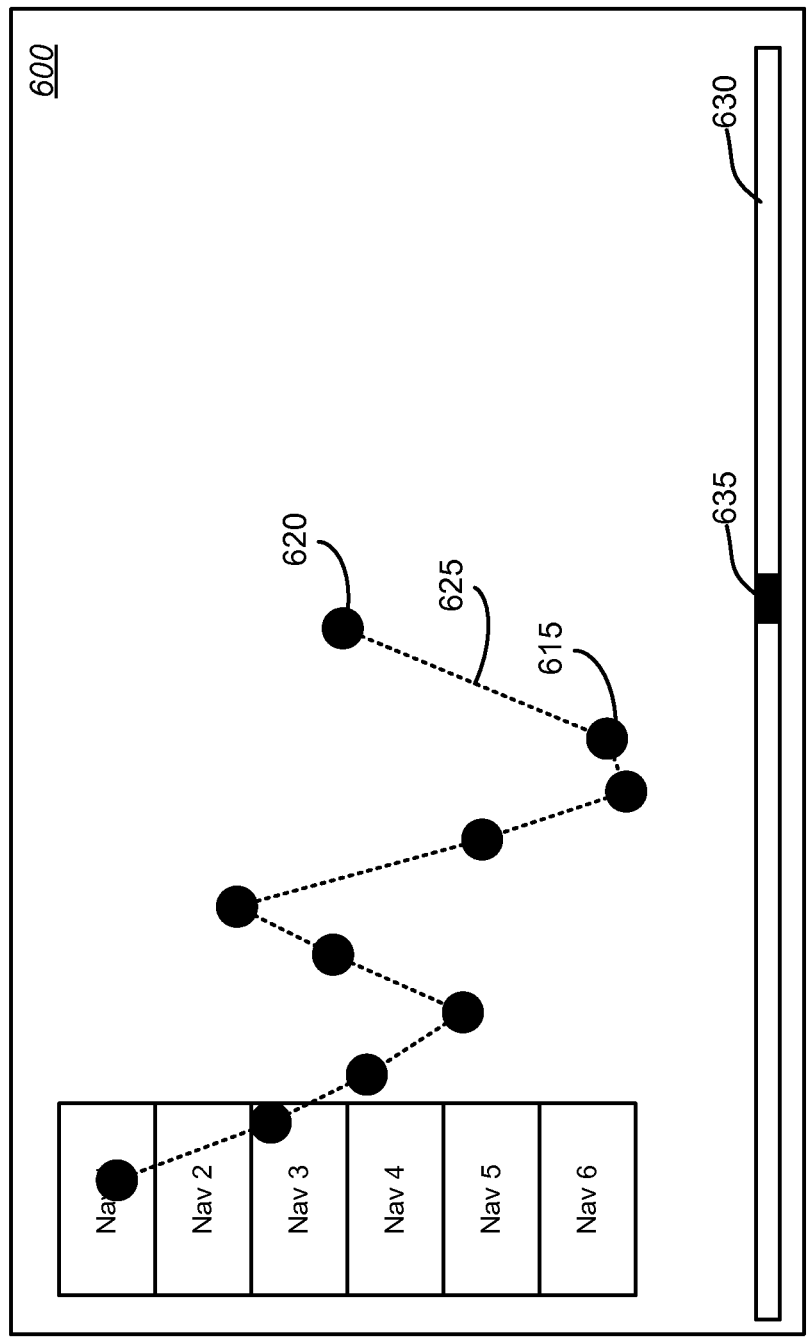

TIME EXPANSION FOR DISPLAYING PATH INFORMATION

CROSS-REFERENCES TO RELATED APPLICATIONS

The present application claims benefit under 35 USC 119(e) of U.S. Provisional Application No. 61/113,538, filed on Nov. 11, 2008, entitled "Techniques For Analyzing Paths," the entire contents of which are incorporated herein by reference for all purposes. The present application is also related to U.S. patent application Ser. No. 12/615,736 entitled "Finding Sequential Matches in Eye Tracking Data" and U.S. patent application Ser. No. 12/615,749 entitled "Using Dotplots for Comparing and Finding Patterns in Sequences of Data Points" both of which are filed concurrently herewith and incorporated herein by reference for all purposes.

BACKGROUND

Embodiments of the present invention relate to analyzing sequential data, and more specifically to an expandable display of sequential information representing a path.

Analysis of paths is performed in various different fields or domains. For example, in eye tracking analysis, scanpaths representing users' eye movements while viewing a scene may be analyzed to determine high-level scanning strategies. The scanning strategies determined from such an analysis may be used to improve product designs. For example, by studying scanpaths for users viewing a web page, common viewing trends may be determined and used to improve the web page layout. Various other types of analyses on paths may be performed in other fields. Accordingly, new and improved techniques are always desirable for analyzing and displaying path-related information that can provide insight into characteristics of the path and that facilitate comparisons of paths.

BRIEF SUMMARY

Embodiments of the present invention provide systems and methods for displaying sequential information representing a path. The sequential information can include a number of tokens representing a path. A representation of the tokens and path of the sequential information can be displayed. An instruction to adjust the representation of the path of the sequential information can be received. For example, instruction can comprise user instruction, including but not limited to a user manipulation of a slider control of a user interface through which the representation of the sequence is displayed. The displayed representation of the path of the sequential information can be updated based on and corresponding to the instruction. So for example, the user can click and drag or otherwise manipulate the slider control above and the displayed representation of the path can be expanded and/or contracted based on the user's movement of the slider control. In other words, embodiments of the present invention provide an interactive display that vertically or horizontally separates the displayed tokens and the path of the sequential information to make it easier for the user to trace the sequentially ordered tokens in the paths.

According to one embodiment, a method for displaying sequential information can comprise plotting a plurality of tokens of the sequential information on a first axis and a second axis. The plurality of tokens of the sequential information can represent a path, the first axis can represent a spatial relationship between the tokens, and the second axis can represent a combination of a spatial relationship between the tokens and a relative temporal order of the tokens within the sequence. A representation of the path of the sequential information can be displayed based on plotting the tokens of the sequential information on the first axis and the second axis.

An instruction to adjust the representation of the path of the sequential information can be received. The instruction can comprise a user instruction. For example, the user instruction can comprise user manipulation of a slider control of a user interface through which the representation of the sequence is displayed. A ratio between the spatial relationship and relative temporal order of the tokens represented along the second axis can be adjusted based on the instruction. The tokens of the sequential information can be re-plotted on the first and second axis based on the adjusted ratio between the spatial relationship and relative temporal order of the tokens representing along the second axis. The displayed representation of the path of the sequential information can be updated based on re-plotting the tokens of the sequential information on the first axis and the second axis.

For example, the instruction to adjust the representation of the path of the sequential data can comprise an instruction to expand the representation. In such a case, adjusting the ratio between the spatial relationship and relative temporal order of the tokens represented along the second axis can comprise increasing a contribution of each token to the ratio between the spatial relationship and relative temporal order of the tokens representing along the second axis. Alternatively, the instruction to adjust the representation of the path of the sequential data can comprise an instruction to contract the representation. In such a case, adjusting the ratio between the spatial relationship and relative temporal order of the tokens represented along the second axis can comprise decreasing a contribution of each token to the ratio between the spatial relationship and relative temporal order of the tokens representing along the second axis.

According to another embodiment, a system for displaying sequential information can comprise a display device, a processor communicatively coupled with the display device, and a memory communicatively coupled with and readable by the processor. The memory can have stored therein a series of instructions which, when executed by the processor, cause the processor to plot a plurality of tokens of the sequential information on a first axis and a second axis. The plurality of tokens of the sequential information can represent a path, the first axis can represent a spatial relationship between the tokens, and the second axis can represent a combination of a spatial relationship between the tokens and a relative temporal order of the tokens within the sequence. A representation of the path of the sequential information can be displayed based on plotting the tokens of the sequential information on the first axis and the second axis. An instruction to adjust the representation of the path of the sequential information can be received. The instruction can comprise a user instruction. For example, the user instruction can comprise user manipulation of a slider control of a user interface through which the representation of the sequence is displayed. A ratio between the spatial relationship and relative temporal order of the tokens represented along the second axis can be adjusted based on the instruction. The tokens of the sequential information can be re-plotted on the first and second axis based on the adjusted ratio between the spatial relationship and relative temporal order of the tokens representing along the second axis. The displayed representation of the path of the sequential information can be updated based on re-plotting the tokens of the sequential information on the first axis and the second axis.

According to yet another embodiment, a machine-readable medium can have stored thereon a series of instructions which, when executed by a processor, cause the processor to display sequential information by plotting a plurality of tokens of the sequential information on a first axis and a second axis. The plurality of tokens of the sequential information can represent a path, the first axis can represent a spatial relationship between the tokens, and the second axis can represent a combination of a spatial relationship between the tokens and a relative temporal order of the tokens within the sequence. A representation of the path of the sequential information can be displayed based on plotting the tokens of the sequential information on the first axis and the second axis. An instruction to adjust the representation of the path of the sequential information can be received. The instruction can comprise a user instruction. For example, the user instruction can comprise user manipulation of a slider control of a user interface through which the representation of the sequence is displayed. A ratio between the spatial relationship and relative temporal order of the tokens represented along the second axis can be adjusted based on the instruction. The tokens of the sequential information can be re-plotted on the first and second axis based on the adjusted ratio between the spatial relationship and relative temporal order of the tokens representing along the second axis. The displayed representation of the path of the sequential information can be updated based on re-plotting the tokens of the sequential information on the first axis and the second axis.

BRIEF DESCRIPTION OF THE DRAWINGS

FIGS. 6A and 6B illustrate another example of time expansion for displaying path information according to one embodiment of the present invention.

DETAILED DESCRIPTION

Figure 1:
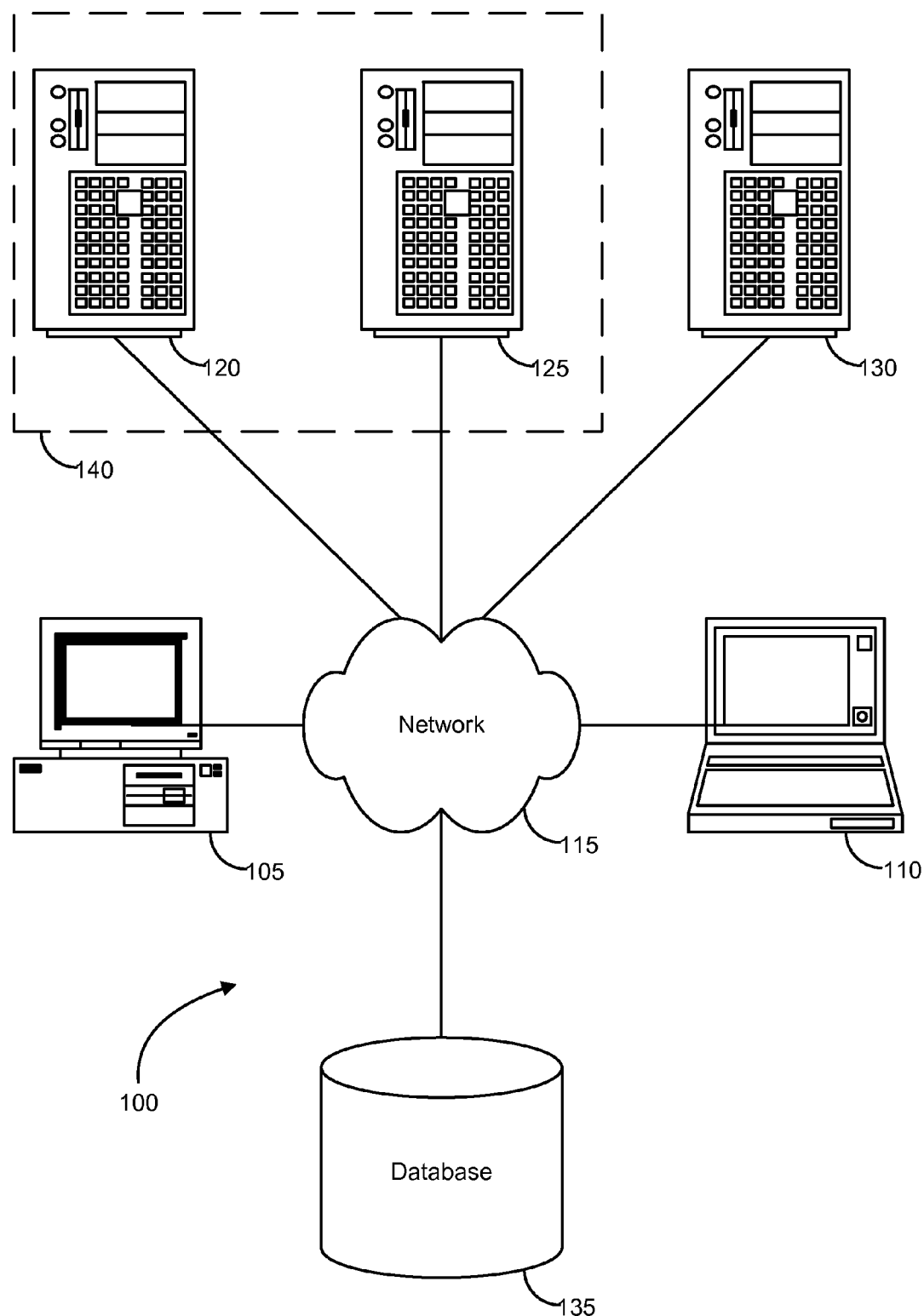
FIG. 1 is a block diagram illustrating components of an exemplary operating environment in which various embodiments of the present invention may be implemented.

In the following description, for the purposes of explanation, numerous specific details are set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Embodiments of the present invention provide systems and methods for displaying sequential data representing paths such as eye tracking data including scanpaths representing users' eye movements while viewing a stimulus image or other scene. As the term is used herein, a path may be defined as a sequence of two or more points. The first point in the sequence of points may be referred to as the start point of the path and the last point in the sequence may be referred to as the end point of the path. The portion of a path between any two consecutive points in the sequence of points may be referred to as a path segment. A path may comprise one or more segments.

A sequence may be any list of tokens or symbols in a particular order. Examples of sequences can include but are not limited to words in a query, words in a document, symbols in a computer program's source code, scanpaths, i.e., sequences of eye tracking fixation points as determined by an eye tracking system, sequences of requested URLs in a user's web browsing session, sequences of requested URLs in a web server's log file, etc.

Thus, there are different types of paths considered to be within the scope of the term as used herein. Examples described below have been described with reference to a specific type of path, referred to as a scanpath, which is used to track eye movements. A scanpath is a path that an eye follows when viewing a scene. A scanpath is defined by a sequence of fixation points (or gaze locations). A path segment between two consecutive fixation points in the sequence of fixation points is referred to as a saccade. A scanpath is thus a sequence of fixation points connected by saccades during scene viewing where the saccades represent eye movements between fixation points. For purposes of simplicity, the scanpaths described below are 2-dimensional paths. The teachings of the present invention may however also be applied to paths in multiple dimensions.

Embodiments of the present invention provide systems and methods for displaying sequential information representing a path. The sequential information can include a number of tokens representing a path. The plurality of tokens of the sequential information can be plotted on a first axis and a second axis. The first axis can represent a spatial relationship between the tokens within the path and the second axis can represent a relative temporal order of the tokens within the sequence. A representation of the path of the sequential information can be displayed based on plotting the tokens of the sequential information on the first axis and the second axis. An instruction to adjust the representation of the path of the sequential information can be received. For example, the instruction can comprise a user instruction such as a user manipulation of a slider control of a user interface through which the representation of the sequence is displayed. The tokens of the sequential information can be re-plotted on the first and second axis based on the instruction. and the displayed representation of the path of the sequential information can be updated based on re-plotting the tokens of the sequential information on the first axis and the second axis. That is, the displayed representation of the path can be updated or adjusted based on and corresponding to the instruction.

It should be understood that, while embodiments of the present invention have been described in context of scanpaths, this is not intended to limit the scope of the present invention as recited in the claims to scanpaths. Teachings of the present invention may also be applied to other types of paths occurring in various different domains such as a stock price graph, a path followed by a car between a start and an end destination, and the like. Various additional details of embodiments of the present invention will be described below with reference to the figures.

FIG. 1 is a block diagram illustrating components of an exemplary operating environment in which various embodiments of the present invention may be implemented. The system 100 can include one or more user computers 105, 110, which may be used to operate a client, whether a dedicate application, web browser, etc. The user computers 105, 110 can be general purpose personal computers (including, merely by way of example, personal computers and/or laptop computers running various versions of Microsoft Corp.'s Windows and/or Apple Corp.'s Macintosh operating systems) and/or workstation computers running any of a variety of commercially-available UNIX or UNIX-like operating systems (including without limitation, the variety of GNU/Linux operating systems). These user computers 105, 110 may also have any of a variety of applications, including one or more development systems, database client and/or server applications, and web browser applications. Alternatively, the user computers 105, 110 may be any other electronic device, such as a thin-client computer, Internet-enabled mobile telephone, and/or personal digital assistant, capable of communicating via a network (e.g., the network 115 described below) and/or displaying and navigating web pages or other types of electronic documents. Although the exemplary system 100 is shown with two user computers, any number of user computers may be supported.

In some embodiments, the system 100 may also include a network 115. The network may can be any type of network familiar to those skilled in the art that can support data communications using any of a variety of commercially-available protocols, including without limitation TCP/IP, SNA, IPX, AppleTalk, and the like. Merely by way of example, the network 115 may be a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth protocol known in the art, and/or any other wireless protocol); and/or any combination of these and/or other networks such as GSM, GPRS, EDGE, UMTS, 3G, 2.5 G, CDMA, CDMA2000, WCDMA, EVDO etc.

The system may also include one or more server computers 120, 125, 130 which can be general purpose computers and/or specialized server computers (including, merely by way of example, PC servers, UNIX servers, mid-range servers, mainframe computers rack-mounted servers, etc.). One or more of the servers (e.g., 130) may be dedicated to running applications, such as a business application, a web server, application server, etc. Such servers may be used to process requests from user computers 105, 110. The applications can also include any number of applications for controlling access to resources of the servers 120, 125, 130.

The web server can be running an operating system including any of those discussed above, as well as any commercially-available server operating systems. The web server can also run any of a variety of server applications and/or mid-tier applications, including HTTP servers, FTP servers, CGI servers, database servers, Java servers, business applications, and the like. The server(s) also may be one or more computers which can be capable of executing programs or scripts in response to the user computers 105, 110. As one example, a server may execute one or more web applications. The web application may be implemented as one or more scripts or programs written in any programming language, such as Java™, C, C# or C++, and/or any scripting language, such as Perl, Python, or TCL, as well as combinations of any programming/scripting languages. The server(s) may also include database servers, including without limitation those commercially available from Oracle®, Microsoft®, Sybase®, IBM® and the like, which can process requests from database clients running on a user computer 105, 110.

In some embodiments, an application server may create web pages dynamically for displaying on an end-user (client) system. The web pages created by the web application server may be forwarded to a user computer 105 via a web server. Similarly, the web server can receive web page requests and/ or input data from a user computer and can forward the web page requests and/or input data to an application and/or a database server. Those skilled in the art will recognize that the functions described with respect to various types of servers may be performed by a single server and/or a plurality of specialized servers, depending on implementation-specific needs and parameters.

The system 100 may also include one or more databases 135. The database(s) 135 may reside in a variety of locations. By way of example, a database 135 may reside on a storage medium local to (and/or resident in) one or more of the computers 105, 110, 115, 125, 130. Alternatively, it may be remote from any or all of the computers 105, 110, 115, 125, 130, and/or in communication (e.g., via the network 120) with one or more of these. In a particular set of embodiments, the database 135 may reside in a storage-area network ("SAN") familiar to those skilled in the art. Similarly, any necessary files for performing the functions attributed to the computers 105, 110, 115, 125, 130 may be stored locally on the respective computer and/or remotely, as appropriate. In one set of embodiments, the database 135 may be a relational database, such as Oracle 10g, that is adapted to store, update, and retrieve data in response to SQL-formatted commands.

Figure 2:
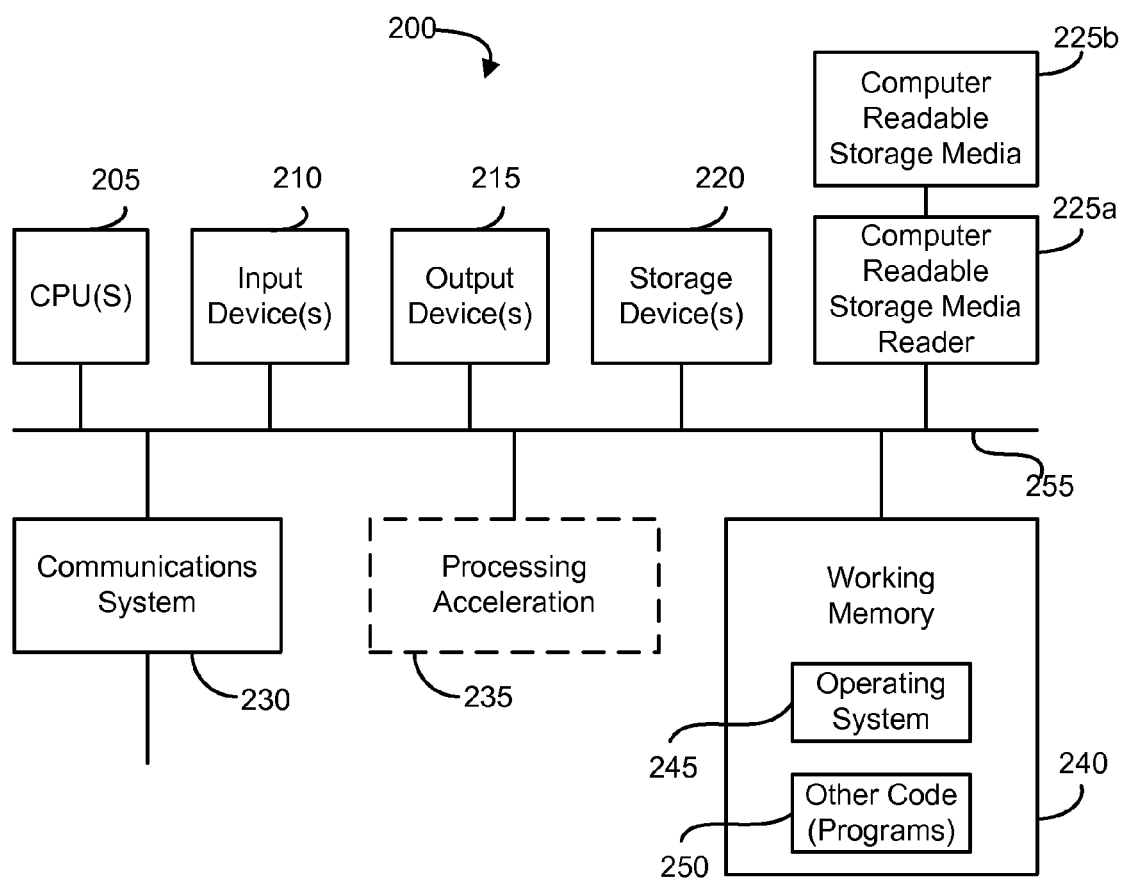
FIG. 2 is a block diagram illustrating an exemplary computer system in which embodiments of the present invention may be implemented.

FIG. 2 illustrates an exemplary computer system 200, in which various embodiments of the present invention may be implemented. The system 200 may be used to implement any of the computer systems described above. The computer system 200 is shown comprising hardware elements that may be electrically coupled via a bus 255. The hardware elements may include one or more central processing units (CPUs) 205, one or more input devices 210 (e.g., a mouse, a keyboard, etc.), and one or more output devices 215 (e.g., a display device, a printer, etc.). The computer system 200 may also include one or more storage device 220. By way of example, storage device(s) 220 may be disk drives, optical storage devices, solid-state storage device such as a random access memory ("RAM") and/or a read-only memory ("ROM"), which can be programmable, flash-updateable and/or the like.

The computer system 200 may additionally include a computer-readable storage media reader 225a, a communications system 230 (e.g., a modem, a network card (wireless or wired), an infra-red communication device, etc.), and working memory 240, which may include RAM and ROM devices as described above. In some embodiments, the computer system 200 may also include a processing acceleration unit 235, which can include a DSP, a special-purpose processor and/or the like.

The computer-readable storage media reader 225a can further be connected to a computer-readable storage medium 225b, together (and, optionally, in combination with storage device(s) 220) comprehensively representing remote, local, fixed, and/or removable storage devices plus storage media for temporarily and/or more permanently containing computer-readable information. The communications system 230 may permit data to be exchanged with the network 220 and/or any other computer described above with respect to the system 200.

The computer system 200 may also comprise software elements, shown as being currently located within a working memory 240, including an operating system 245 and/or other code 250, such as an application program (which may be a client application, web browser, mid-tier application, RDBMS, etc.). It should be appreciated that alternate embodiments of a computer system 200 may have numerous variations from that described above. For example, customized hardware might also be used and/or particular elements might be implemented in hardware, software (including portable software, such as applets), or both. Further, connection to other computing devices such as network input/output devices may be employed. Software of computer system 200 may include code 250 for implementing embodiments of the present invention as described herein.

As noted above, embodiments of the present invention provide for displaying sequential data representing paths such as eye tracking data including scanpaths representing users' eye movements while viewing a stimulus image or other scene. The eye tracking data can represent a number of different scanpaths and can be displayed, for example, to view and/or analyze results obtained from a number of users viewing a user interface or other displayed image so that a layout of a user interface can be evaluated. According to one embodiment, displaying eye tracking data with a path analysis system such as the computer system 200 described above can comprise receiving the eye tracking data at the path analysis system. The eye tracking data, which can be obtained by the system in a number of different ways as will be described below, can include a plurality of scanpaths, each scanpath representing a sequence of regions of interest on a scene such as a stimulus image displayed by the system.

Figure 3:
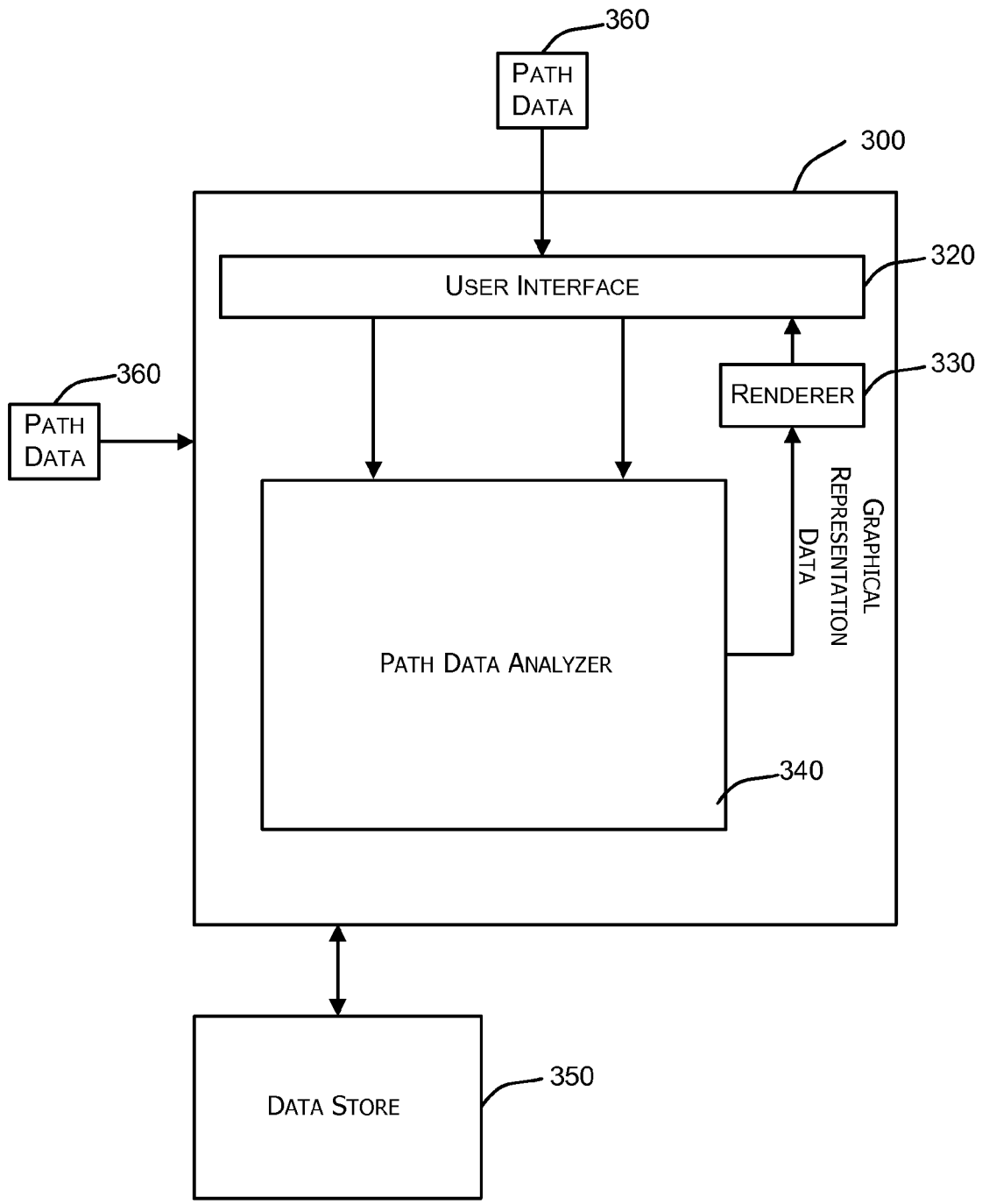
FIG. 3 is a block diagram illustrating, at a high-level, functional components of a system for obtaining and displaying eye tracking data according to one embodiment of the present invention.

FIG. 3 is a block diagram illustrating, at a high-level, functional components of a system for obtaining and/or displaying eye tracking data according to one embodiment of the present invention. In this example, the path analysis system 300 comprises several components including a user interface 320, a renderer 330, and a path data analyzer 340. The various components may be implemented in hardware, or software (e.g., code, instructions, program executed by a processor), or combinations thereof. Path analysis system 300 may be coupled to a data store 350 that is configured to store data related to processing performed by system 300. For example, path data (e.g., scanpath data) may be stored in data store 350.

User interface 320 provides an interface for receiving information from a user of path analysis system 300 and for outputting information from path analysis system 300. For example, a user of path analysis system 300 may enter path data 360 for a path to be analyzed via user interface 320. Additionally or alternatively, a user of path analysis system 300 may enter commands or instructions via user interface 320 to cause path analysis system 300 to obtain or receive path data 360 from another source.

System 300 may additionally or alternatively receive path data 360 from various other sources. In one embodiment, the path data may be received from sources such as from an eye tracker device. For example, information regarding the fixation points and saccadic eye movements between the fixation points, i.e., path data 360, may be gathered using eye tracking devices such as devices provided by Tobii (e.g., Tobii T60 eye tracker). An eye-tracking device such as the Tobii T60 eye tracker is capable of capturing information related to the saccadic eye activity including location of fixation points, fixation durations, and other data related to a scene or stimulus image, such as a webpage for example, while the user views the scene. Such an exemplary user interface is described in greater detail below with reference to FIG. 4 The Tobii T60 uses infrared light sources and cameras to gather information about the user's eye movements while viewing a scene.

The path data may be received in various formats, for example, depending upon the source of the data. In one embodiment and regardless of its exact source and/or format, path data 360 received by system 300 may be stored in data store 350 for further processing.

Path data 360 received by system 300 from any or all of these sources can comprise data related to a path or plurality of paths to be analyzed by system 300. Path data 360 for a path may comprise information identifying a sequence of points included in the path, and possibly other path related information. For example, for a scanpath, path data 360 may comprise information related to a sequence of fixation points defining the scanpath. Path data 360 may optionally include other information related to a scanpath such as the duration of each fixation point, inter-fixation angles, inter-fixation distances, etc. Additional details of exemplary scanpaths as they relate to an exemplary stimulus image are described below with reference to FIG. 4.

Path analysis system 300 can also include path data analyzer 340 and renderer 330. Path data analyzer 340 and renderer 330 can be configured to receive the path data 360 and provide, e.g., via user interface 320, a display or other representation of the scanpaths. For example, renderer 330 may provide a graphical representation of the scanpaths on a chart or graph. Additionally or alternatively, renderer 330 may provide a graphical representation of the scene or stimulus image for which the eye tracking data was obtained with a representation of the scanpaths presented thereon as illustrated in and described in greater detail below with reference to FIGS. 4-6.

As noted above, the path data 360, i.e., information regarding the fixation points and saccadic eye movements between the fixation points, may be gathered using eye tracking devices such as devices capable of capturing information related to the saccadic eye activity including location of fixation points, fixation durations, and other data related to a scene or stimulus image while the user views the scene or image. Such a stimulus image can comprise, for example, a webpage or other user interface which, based on analysis of various scanpaths may be evaluated for possible improvements to the format or layout thereof.

Figure 4:
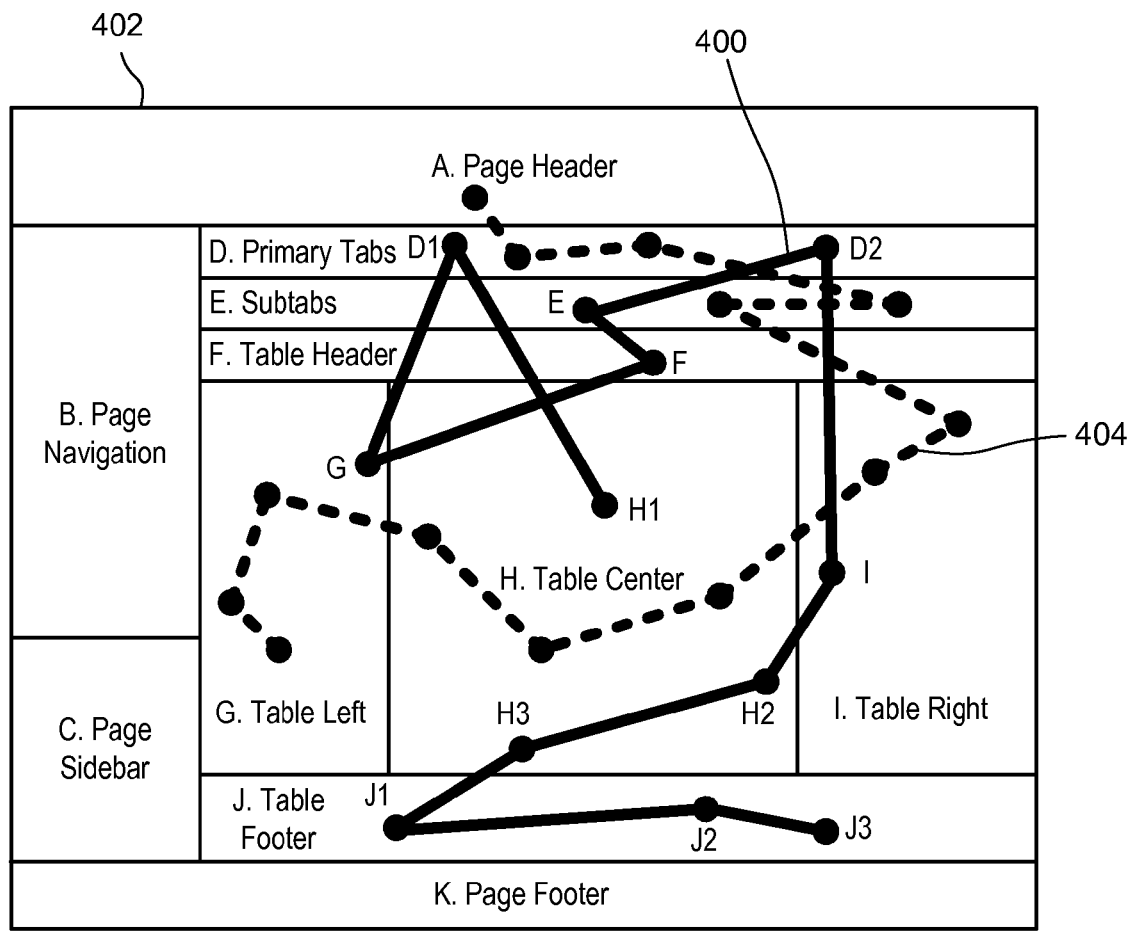
FIG. 4 illustrates an exemplary stimulus image of a user interface which may be used with embodiments of the present invention and a number of exemplary scanpaths.

FIG. 4 illustrates an exemplary stimulus image of a user interface which may be used with embodiments of the present invention and a number of exemplary scanpaths. It should be noted that this stimulus image and user interface are provided for illustrative purposes only and are not intended to limit the scope of the present invention. Rather, any number of a variety of different stimulus images, user interfaces, or means and/or methods of obtaining a query sequence are contemplated and considered to be within the scope of the present invention.

In this example, the image, which can comprise for example a web page 402 or other user interface of a software application, includes a number of elements which each, or some of which, can be considered a particular region of interest. For example, webpage 402 may be considered to comprise multiple regions such as: A (page header), B (page navigation area), C (page sidebar), D (primary tabs area), E (subtabs area), F (table header), G (table left), H (table center), I (table right), J (table footer), and K (page footer). Webpage 402 may be displayed on an output device such as a monitor and viewed by the user.

FIG. 4 also depicts exemplary scanpaths 400 and 404 representing eye movements of one or more users while viewing the webpage 402 and obtained or captured by an eye tracking device as described above. Paths 400 and 404 shows the movements of the users' eyes across the various regions of page 402. The circles depicted in FIG. 4 represent fixation points. A fixation point marks a location in the scene where the saccadic eye movement stops for a brief period of time while viewing the scene. In some cases, a fixation point can be represented by, for example, a label or name identifying a region of interest of the page in which the fixation occurs. So for example, scanpath 400 depicted in FIG. 4 may be represented by the following sequence of region names {H, D, G, F, E, D, I, H, H, J, J, J}.

The scanpath data gathered by an eye tracker can be used with embodiments of the present invention to, for example, display the path data. That is, a set of path data 360 representing multiple scanpaths can be obtained by the system 300 and displayed via user interface 320. the displayed image can include a copy or representation of the stimulus image 402 with representations of the scanpaths 400 and 404 displayed thereon. While the paths illustrated in FIG. 4 represent paths spanning a large portion of the stimulus image, it should be understood that using other stimulus images may provide different results. For example, in an image comprising a number of regions of interest that are arranged in a largely horizontal or vertical fashion, a user may scan back and forth, or up and down, across these regions. The resulting paths would thus be relatively narrow and long which can cause a displayed representation of such paths difficult to discern. Additionally, if multiple paths are represented at the same time, i.e., displayed on the same representation of the stimulus image, the problem is compounded and the paths and fixations may quickly become unrecognizable and unintelligible.

Thus, embodiments of the present invention provide for expanding such displayed representations of path data to provide for vertically and/or horizontally separating fixations or other tokens in the displayed paths to make it easier for the user to trace or recognize sequentially ordered tokens within the paths. According to one embodiment, a display of path information, such as the example illustrated in FIG. 4, can be adapted to include a control, for example in the form of a slider or other element, that allows a user to manipulate the image to expand and/or contract the displayed paths. So for example, the user can click and drag or otherwise manipulate the slider control and the displayed representation of the path can be expanded and/or contracted based on the user's movement of the slider control.

Figure 5A:
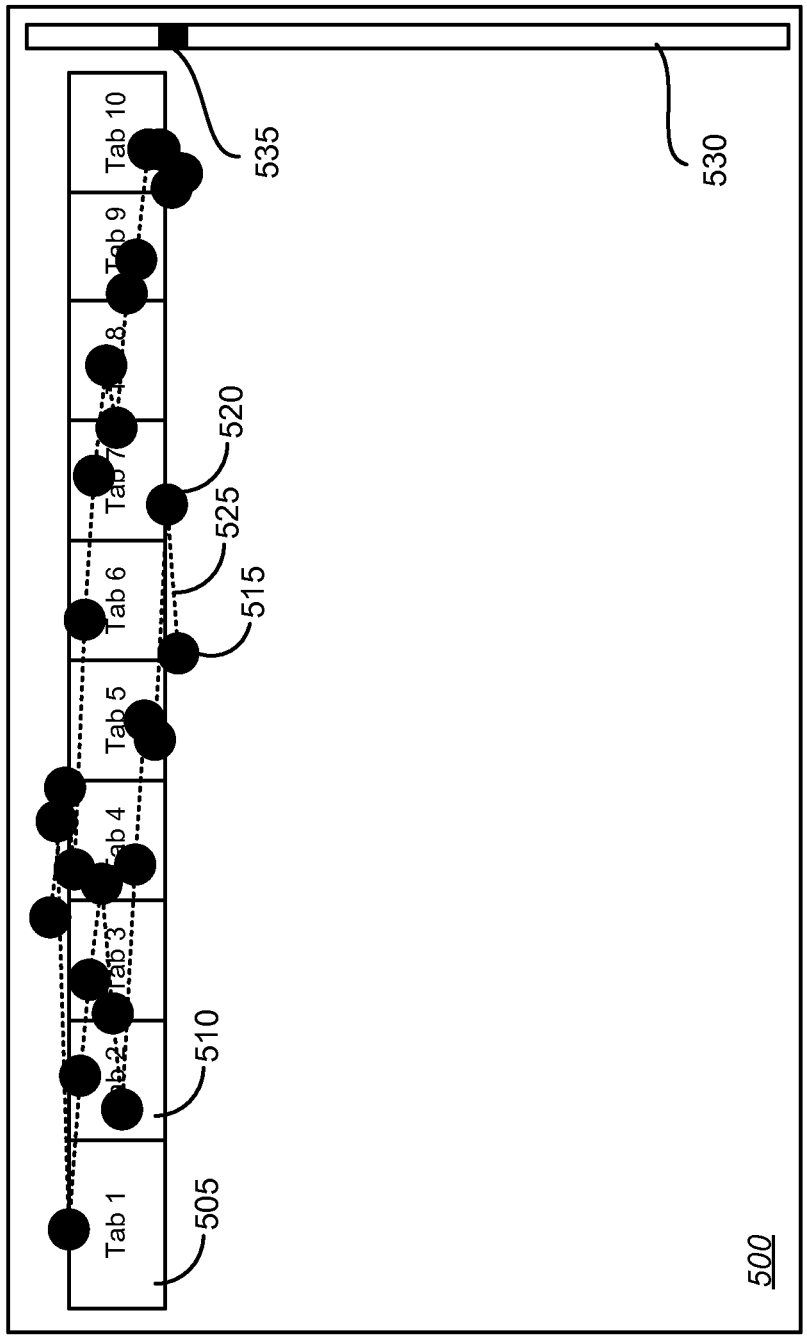
FIGS. 5A and 5B illustrate an example of time expansion for displaying path information according to one embodiment of the present invention.
Figure 5B:
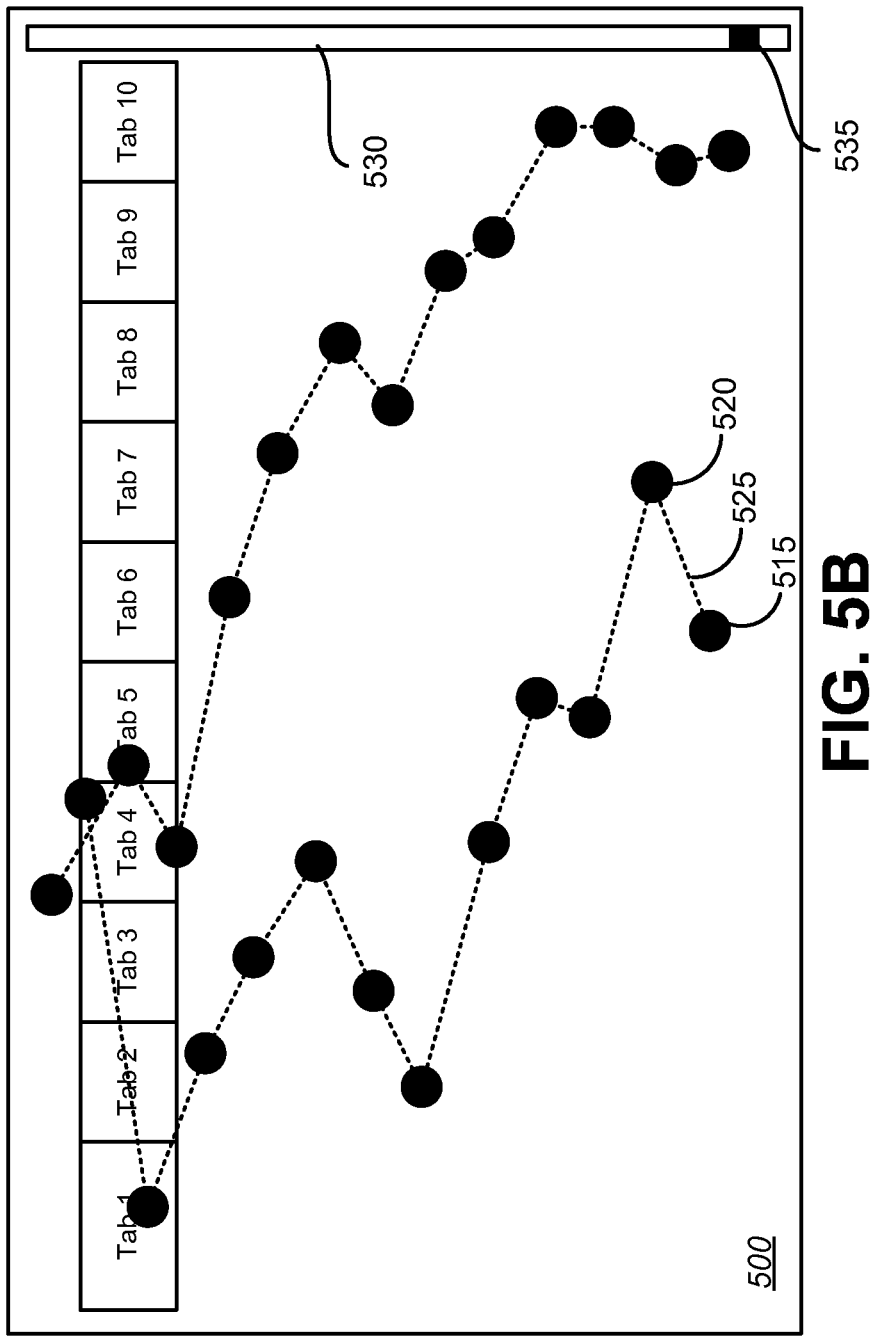

FIGS. 5A and 5B illustrate an example of time expansion for displaying path information according to one embodiment of the present invention. More specifically, this example illustrates a page 500, e.g., a web page, window, etc., of a user interface through which can be displayed a representation of copy of a stimulus image or portion thereof. For example, page 500 includes a number of elements comprising tab markers 505 and 510 arranged horizontally across the page 500. Page 500 also includes a number of fixations, e.g., 515 and 520, and connecting saccades, e.g., 525 making up scanpaths. In FIG. 5A, these paths are shown clustered about the tab markers as would be the case as users' eyes scan left and right reading the various tab markers. As can be seen, the representation of the scanpaths displayed is difficult to use to identify or trace the scanpaths presented therein.

According to one embodiment, the page 500 also includes a control, in this example illustrated as a slider control consisting of bar 530 and slider 535. Through manipulation of a mouse or other pointing device, touch screen, keyboard or other input device, the user viewing page 500 can select and move the slider 535 along the bar 530 of the slider control. So for example, as illustrated in FIG. 5B, moving slider 535 down bar 530 toward the bottom of page 500 causes the representation of the scanpaths to expand toward the bottom of page 500 so that fixations 515 and 520 and saccades 525 as well as the overall scanpaths displayed become more easily viewed. According to one embodiment, user manipulation of a mouse or other input device to select and move slider 535 back up bar 530 can correspondingly cause the displayed representations of the scanpaths to contract back toward the tab markers at the top of page 500, i.e., returning toward the representation of FIG. 5A.

FIGS. 6A and 6B illustrate another example of time expansion for displaying path information according to one embodiment of the present invention. This example illustrates a similar page 600 but with a number of navigation elements, e.g., 605 and 610, displayed vertically along the left side of the page. Again, a number of fixations, e.g., 615 and 620, and connecting saccades, e.g., 625 making up scanpaths are also displayed on page 600. In FIG. 6A, these paths are shown clustered about the navigation elements as would be the case as users' eyes scan up and down reading the various elements.

Page 600 also includes a slider control consisting of bar 630 and slider 635. Through manipulation of a mouse or other pointing device, touch screen, keyboard or other input device, the user viewing page 600 can select and move the slider 635 along the bar 630 of the slider control. So for example, as illustrated in FIG. 6B, moving slider 635 right along bar 630 toward the right side of page 600 causes the representation of the scanpaths to expand toward the right side of page 600 so that fixations 615 and 620 and saccades 625 as well as the overall scanpaths displayed become more easily viewed. According to one embodiment, user manipulation of a mouse or other input device to select and move slider 635 left along bar 630 can correspondingly cause the displayed representations of the scanpaths to contract back toward the navigation elements at the left side of page 600, i.e., returning toward the representation of FIG. 6A.

Stated another way, one embodiment of the present invention includes a slider control that vertically or horizontally separates tokens such as fixations to make it easier for the user to trace sequentially ordered paths such as scanpaths. This separation or expansion, and conversely, contraction, can be considered to be time based in the sense that it can be considered to expand or contract the representation of the paths based on the relative temporal order of the tokens but while maintaining their relative spatial relationships, i.e., horizontally or vertically depending upon the implementation.

To achieve this expansion, the tokens of the sequential information can be plotted on a first axis and a second axis. The first axis can represent a spatial relationship between the tokens within the path. So for example, in the case of FIGS. 5A and 5B, the first axis may be the horizontal axis that may run along the top of page 500. However, in the example of FIGS. 6A and 6B, the first axis may be the vertical axis running along the left side of page 600. The second axis can represent a relative temporal order of the tokens within the sequence. For example, in the case of FIGS. 5A and 5B, the second axis may be the vertical axis that may run along the left side of page 500. However, in the example of FIGS. 6A and 6B, the second axis may be the horizontal axis running along the top of page 600.

Regardless of the exact orientation of the first and second axis, a representation of the path of the sequential information, e.g., fixations 515, 520, 615, and 620 and saccades 525 and 625, can be displayed, e.g., on pages 500 and 600, based on plotting the tokens of the sequential information on the first axis and the second axis. An instruction to adjust the representation of the path of the sequential information can be received, for example, by a user's manipulation of slider control of the user interface through which the representation of the sequence is displayed. The tokens of the sequential information can be re-plotted on the first and second axis based on the instruction. For example, the instruction to adjust the representation of the path of the sequential data can comprise an instruction to expand the representation such as when the user moves slider 500 down bar 530 toward the bottom of page 500 as illustrated by FIGS. 5A and 5B. In such a case, re-plotting the tokens of the sequential information on the first and second axis based on the instruction can comprise increasing a distance between tokens along the second axis, i.e., the vertical axis of page 500. Conversely, the instruction to adjust the representation of the path of the sequential data can comprise an instruction to contract the representation such as when the user moves slider 500 back up bar 530 toward the top of page 500. In such instance, re-plotting the tokens of the sequential information on the first and second axis based on the instruction can comprise decreasing a distance between tokens along the second axis, i.e., the vertical axis of page 500.

In one embodiment the instruction to adjust the representation of the path of the sequential data can comprise changing the proportion of values contributing to the position of each token. In FIGS. 5a and 5b, for example, re-plotting the tokens of the sequential information on the first and second axis based on the instruction can comprise reducing the contribution of each token's vertical position as determined by the actual path position, while increasing the contribution of each token's temporal position. The vertical position, y, of each token is a function of $y=x*Sy+Ty/x$, where Sy is the token's vertical position as determined by the actual path poison, Ty is token's temporal position, and x is a factor that can correspond to a slider position. In FIGS. 6a and 6b, re-plotting the tokens of the sequential information on the first and second axis based on the instruction can comprise reducing the contribution of each token's horizontal position as determined by the actual path position, while increasing the contribution of each token's temporal position. In either case, the displayed representation of the path of the sequential information can be updated based on re-plotting the tokens of the sequential information on the first axis and the second axis.

It should be understood that the examples illustrated in FIGS. 5A-6B are provided for illustrative purposes only and are not intended to limit the scope of the present invention. Rather, it should be understood that, depending upon the exact implementations, various other interface, controls, and/or graphical of other representations of sequential information as well as other changes may by made without departing from the scope of the present invention. For example, while only two paths are illustrated in FIGS. 5A and 5B and only one path is illustrated in FIGS. 6A and 6B for the sake of clarity, is should be understood that many more paths may be represented in actual implementations. Also, as noted above, embodiments of the present invention are not limited to representations of scanpaths and fixations, i.e., eye tracking data. Rather, any of a variety of other types of sequential information may be represented in other implementations. Importantly, embodiments of the present invention are not limited to a particular user interface or even control type. For example, in other cases, the instructions to expand or contract the displayed representation(s) of one or more paths may be based on a user manipulating an up and/or down arrow key or other keys of a keyboard, touching or clicking a button or buttons of a user interface, or otherwise interacting with the user interface through which the representation of the sequence is displayed.

Figure 7:
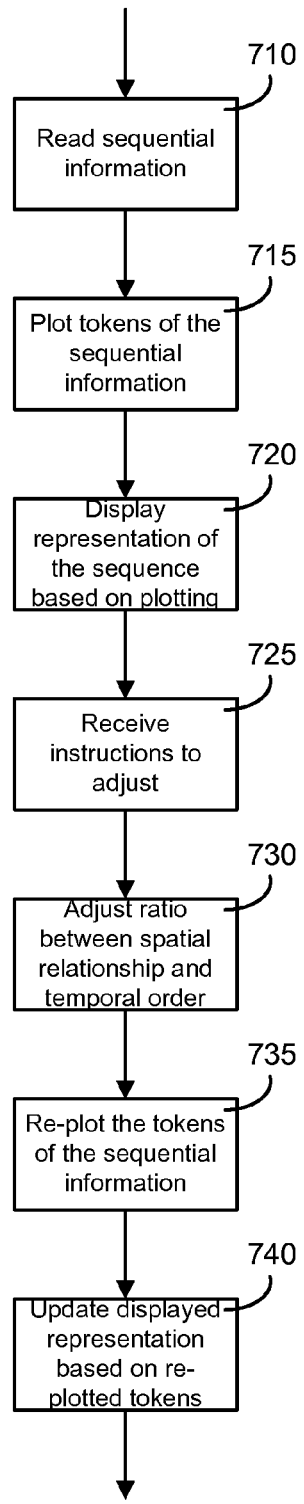
FIG. 7 is a flowchart illustrating a process for time expansion for displaying path information according to one embodiment of the present invention.

FIG. 7 is a flowchart illustrating a process for time expansion for displaying path information according to one embodiment of the present invention. In this example, the process begins with reading 710 a set of sequential information. As explained above, the sequential information can include a number of tokens representing a path such as, but not limited to, a scanpath. The plurality of tokens of the sequential information can be plotted 715 on a first axis and a second axis. The first axis can represent a spatial relationship between the tokens within the path and the second axis can represent a combination of a spatial relationship between the tokens and a relative temporal order of the tokens within the sequence. Depending upon such considerations as the nature and/or orientation of the path, the types of tokens, the eventual use or display of the path information, etc., the axis can be oriented differently. That is, the first axis may comprise a horizontal axis and the second axis may comprise a vertical axis. Alternatively, the first axis may comprise a vertical axis and the second axis may comprise a horizontal axis. Regardless of the exact orientation of the first and second axis, a representation of the path of the sequential information can be displayed 720 based on plotting the tokens of the sequential information on the first axis and the second axis.

An instruction to adjust the representation of the path of the sequential information can be received 725. For example, instruction can comprise user instruction. As described above, such a user instruction can comprise user manipulation of a slider control of a user interface through which the representation of the sequence is displayed. In other cases, the instruction may be based on a user manipulating an up and/or down arrow key or other keys of a keyboard, touching or clicking a button or buttons of a user interface, or otherwise interacting with the user interface through which the representation of the sequence is displayed.

Regardless of how the instruction is received, a ratio between the spatial relationship and relative temporal order of the tokens represented along the second axis can be adjusted 730 based on the instruction. For example, the instruction to adjust the representation of the path of the sequential data can comprise an instruction to expand the representation. In such a case, adjusting 730 the ratio between the spatial relationship and relative temporal order of the tokens represented along the second axis can comprise increasing a contribution of each token to the ratio between the spatial relationship and relative temporal order of the tokens representing along the second axis. Alternatively, the instruction to adjust the representation of the path of the sequential data can comprise an instruction to contract the representation. In such a case, adjusting 730 the ratio between the spatial relationship and relative temporal order of the tokens represented along the second axis can comprise decreasing a contribution of each token to the ratio between the spatial relationship and relative temporal order of the tokens representing along the second axis.

The tokens of the sequential information can be re-plotted 735 on the first and second axis based on the adjusted ration between the spatial relationship and the relative temporal order of the tokens represented along the second axis. The displayed representation of the path of the sequential information can be updated 740 based on re-plotting the tokens of the sequential information on the first axis and the second axis. That is, the displayed representation of the path can be updated or adjusted based on and corresponding to the instruction. So for example, the user can click and drag or otherwise manipulate the slider control described above and the displayed representation of the path can be expanded and/or contracted based on the user's movement of the slider control.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A method for displaying sequential information, the method comprising:
    plotting a plurality of tokens of the sequential information on a first axis and a second axis, wherein the plurality of tokens of the sequential information represent a path, the first axis represents a spatial relationship between the tokens, and the second axis represents a combination of a spatial relationship between the tokens and a relative temporal order of the tokens within the sequence;
    displaying a representation of the path of the sequential information based on plotting the tokens of the sequential information on the first axis and the second axis;
    receiving an instruction to adjust the representation of the path of the sequential information along the second axis, the instruction indicating a change to a time basis of the relative temporal order of the tokens represented by the second axis;
    adjusting a ratio between the spatial relationship and relative temporal order of the tokens represented along the second axis based on the instruction;
    re-plotting the tokens of the sequential information on the first and second axis based on the adjusted ratio between the spatial relationship and relative temporal order of the tokens represented along the second axis; and
    updating the displayed representation of the path of the sequential information based on re-plotting the tokens of the sequential information on the first axis and the second axis.

2. The method of claim 1, wherein the instruction to adjust the representation of the path of the sequential data comprises an instruction to expand the representation and wherein adjusting the ratio between the spatial relationship and relative temporal order of the tokens represented along the second axis comprises increasing a contribution of each token to the ratio between the spatial relationship and relative temporal order of the tokens representing along the second axis.

3. The method of claim 1, wherein the instruction to adjust the representation of the path of the sequential data comprises an instruction to contract the representation and wherein adjusting the ratio between the spatial relationship and relative temporal order of the tokens represented along the second axis comprises decreasing a contribution of each token to the ratio between the spatial relationship and relative temporal order of the tokens representing along the second axis.

4. The method of claim 1, wherein the first axis comprises a horizontal axis and the second axis comprises a vertical axis.

5. The method of claim 4, wherein the user instructions comprise user manipulation of a slider control of a user interface through which the representation of the sequence is displayed.

6. The method of claim 1, wherein the first axis comprises a vertical axis and the second axis comprises a horizontal axis.

7. The method of claim 1, wherein the instruction comprises user instructions.

8. The method of claim 7, wherein displaying the representation of the path of the sequential information comprises displaying the representation of the fixation points and scanpath on a representation of an image to which the eye tracking data corresponds.

9. The method of claim 1, wherein the sequential information comprises eye tracking data and wherein the tokens comprise fixation points and the path represents a scanpath.

10. A system for displaying sequential information, the system comprising:
a display device;
a processor communicatively coupled with the display device; and
a memory communicatively coupled with and readable by the processor and having stored therein a series of instructions which, when executed by the processor, cause the processor to:
plot a plurality of tokens of the sequential information on a first axis and a second axis, wherein the plurality of tokens of the sequential information represent a path, the first axis represents a spatial relationship between the tokens, and the second axis represents a combination of a spatial relationship between the tokens and a relative temporal order of the tokens within the sequence;
display on the display device a representation of the path of the sequential information based on plotting the tokens of the sequential information on the first axis and the second axis;
receive an instruction to adjust the representation of the path of the sequential information along the second axis, the instruction indicating a change to a time basis of the relative temporal order of the tokens represented by the second axis;
adjust a ratio between the spatial relationship and relative temporal order of the tokens represented along the second axis based on the instruction;
re-plot the tokens of the sequential information on the first and second axis based on the adjusted ratio between the spatial relationship and relative temporal order of the tokens represented along the second axis; and
update the displayed representation of the path of the sequential information based on re-plotting the tokens of the sequential information on the first axis and the second axis.

11. The system of claim 10, wherein the instruction to adjust the representation of the path of the sequential data comprises an instruction to expand the representation and wherein adjusting the ratio between the spatial relationship and relative temporal order of the tokens represented along the second axis comprises increasing a contribution of each token to the ratio between the spatial relationship and relative temporal order of the tokens representing along the second axis.

12. The system of claim 10, wherein the instruction to adjust the representation of the path of the sequential data comprises an instruction to contract the representation and wherein adjusting the ratio between the spatial relationship and relative temporal order of the tokens represented along the second axis comprises decreasing a contribution of each token to the ratio between the spatial relationship and relative temporal order of the tokens representing along the second axis.

13. The system of claim 10, further comprising an input device, wherein receiving the instruction to adjust the representation of the path of the sequential information comprises receiving a user instruction via the input device based on user manipulation of a slider control of a user interface through which the representation of the sequence is displayed.

14. The system of claim 10, wherein the sequential information comprises eye tracking data and wherein the tokens comprise fixation points and the path represents a scanpath.

15. The system of claim 14, wherein displaying the representation of the path of the sequential information comprises displaying the representation of the fixation points and scanpath on a representation of an image to which the eye tracking data corresponds.

16. A machine-readable medium having stored thereon a series of instructions which, when executed by a processor, cause the processor to display sequential information by:
plotting a plurality of tokens of the sequential information on a first axis and a second axis, wherein the plurality of tokens of the sequential information represent a path, the first axis represents a spatial relationship between the tokens, and the second axis represents a combination of a spatial relationship between the tokens and a relative temporal order of the tokens within the sequence;
displaying a representation of the path of the sequential information based on plotting the tokens of the sequential information on the first axis and the second axis;
receiving an instruction to adjust the representation of the path of the sequential information along the second axis, the instruction indicating a change to a time basis of the relative temporal order of the tokens represented by the second axis;
adjusting a ratio between the spatial relationship and relative temporal order of the tokens represented along the second axis based on the instruction;
re-plotting the tokens of the sequential information on the first and second axis based on the adjusted ratio between the spatial relationship and relative temporal order of the tokens represented along the second axis; and
updating the displayed representation of the path of the sequential information based on re-plotting the tokens of the sequential information on the first axis and the second axis.

17. The machine-readable medium of claim 16, wherein the instruction to adjust the representation of the path of the sequential data comprises an instruction to expand the representation and wherein adjusting the ratio between the spatial relationship and relative temporal order of the tokens represented along the second axis comprises increasing a contribution of each token to the ratio between the spatial relationship and relative temporal order of the tokens representing along the second axis.

18. The machine-readable medium of claim 16, wherein the instruction to adjust the representation of the path of the sequential data comprises an instruction to contract the representation and wherein adjusting the ratio between the spatial relationship and relative temporal order of the tokens represented along the second axis comprises decreasing a contribution of each token to the ratio between the spatial relationship and relative temporal order of the tokens representing along the second axis.

19. The machine-readable medium of claim 16, wherein the instruction comprises user instructions.

20. The machine-readable medium of claim 19, wherein the user instructions comprise user manipulation of a slider control of a user interface through which the representation of the sequence is displayed.

21. The machine-readable medium of claim 16, wherein the sequential information comprises eye tracking data and wherein the tokens comprise fixation points and the path represents a scanpath.

22. The machine-readable medium of claim 21, wherein displaying the representation of the path of the sequential information comprises displaying the representation of the fixation points and scanpath on a representation of an image to which the eye tracking data corresponds.

* * * * *

UNITED STATES PATENT AND TRADEMARK OFFICE
CERTIFICATE OF CORRECTION

PATENT NO.         : 8,451,272 B2                                    Page 1 of 1
APPLICATION NO.    : 12/615763
DATED              : May 28, 2013
INVENTOR(S)        : Helfman et al.

It is certified that error appears in the above-identified patent and that said Letters Patent is hereby corrected as shown below:

On Title page 2, in column 1, item [56] under "Other Publications", line 26, delete "XI" and insert -- XL --, therefor.

On Title page 2, in column 2, item [56] under "Other Publications", line 19, after ""Location" delete "Location Location".

In the Specification

In column 8, line 57, delete "FIG. 4" and insert -- FIG. 4. --, therefor.

In column 12, line 43, delete "by" and insert -- be --, therefor.

Signed and Sealed this
First Day of October, 2013

Teresa Stanek Rea
*Deputy Director of the United States Patent and Trademark Office*